United States Patent [19]

Stallcup

[11] 4,161,539

[45] Jul. 17, 1979

[54] USE OF MALIC ACID AS A RUMINANT FEED ADDITIVE

[75] Inventor: Odie T. Stallcup, Fayetteville, Ark.

[73] Assignee: The Dow Chemical Company, Midland, Mich.

[21] Appl. No.: 912,694

[22] Filed: Jun. 5, 1978

Related U.S. Application Data

[63] Continuation-in-part of Ser. No. 786,315, Apr. 11, 1977, abandoned.

[51] Int. Cl.$^2$ .............................................. A61K 31/19
[52] U.S. Cl. .................................................. 424/317
[58] Field of Search ........................................ 424/317

[56] References Cited

PUBLICATIONS

Chemical Abstracts, vol. 81, (1974), p. 118987c.
Barr, J. T., Graduate Thesis, "The Influence of Addition of Certain Organic Acids on Nitrogen Metabolism & Energy Digestibility in Holstein Bulls," U. of Ark (1969).

*Primary Examiner*—V. D. Turner

[57] ABSTRACT

Malic acid has been found to be both an effective growth-promoting and feed saving agent for ruminants such as sheep and cattle and, additionally, an effective milk-promoting agent for female ruminants.

11 Claims, No Drawings

USE OF MALIC ACID AS A RUMINANT FEED ADDITIVE

CROSS-REFERENCE TO RELATED APPLICATION

This application is a continuation-in-part of Application Ser. No. 786,315, filed Apr. 11, 1977, now abandoned.

SUMMARY OF THE INVENTION

This invention is concerned with animal husbandry and in particular is concerned with a method of accelerating the growth (i.e. improving the weight gain) of ruminants and/or improving the feed efficiency of said ruminants. This invention is also concerned with a method of improving the milk production of female ruminants such as, for example, dairy cattle. The invention is particularly suitable for use with domestic ruminants maintained on a predetermined ration but may also be used to supplement the diets of ruminants that graze on forage feeds.

In accordance with the present invention, improved growth response, i.e. weight gain, and/or feed efficiency response in ruminants is accomplished by a method which comprises orally administering to the ruminant a growth-promoting amount of malic acid. Also in accordance with the present invention, improved milk production and/or improved feed efficiency response, said improved feed efficiency response being illustrated by improved utilization of concentrate and other standard feeds in milk producing mammals such as dairy cattle, are accomplished by a method which comprises orally administering to the mammel a milk-promoting amount of malic acid.

BACKGROUND OF THE INVENTION

Malic acid, $HOCOHCH_2CH(OH)COOH$, a white triclinic crystalline powder, is well known to be a general-purpose acidulant. It is produced synthetically by catalytic oxidation of benzene to maleic acid, which is converted to malic acid by heating with steam under pressure. The commercial synthetic product is a racemic mixture of the D- and L-isomers. Unless stated otherwise, the term "malic acid" as used in the specification and claims refers to both the DL (racemic) and L forms. Malic acid is approved by the FDA as a GRAS (Generally Recognized As Safe) compound for miscellaneous and/or general-purpose food additive use.

DeVuyst et al. in Revue de d'agriculture, Volume 1, pp. 35–41, January-February 1974, describe a feeding experiment in which 2% (of feed weight) malic acid was added to the weaning feed of milk-fed veal calves. The study concluded that the malic acid did not in any way improve the performance of veal calves under the given experimental conditions. In fact, the growth rate of the calves fed malic acid was 7.5% less than the growth rate of the control group.

J. T. Barr, in a graduate thesis entitled "The Influence of Addition of Certain Organic Acids on Nitrogen Metabolism and Energy Digestibility in Holstein Bulls" (University of Arkansas, Fayetteville, 1969, Library Identification SF/203/B34) describes experiments in which bulls were fed basal diets supplemented by 108.0 g urea and 70.0 g malic acid. The basal diet consisted of 4 kg prairie hay and 1 kg of 87% cane molasses on soybean hulls. It was discovered that there was greater mean nitrogen retention and mean digestibility of crude portein when the bulls were fed a malic acid-supplemented diet than when the bulls were fed identical diets absent the malic acid.

DESCRIPTION OF THE INVENTION

Malic acid has been discovered to be useful as a growth-promoting agent when administered in a growth-promoting amount to the feeds of ruminants such as cattle and sheep. Malic acid has also been discovered to promote increased milk production when it is administered in a milk-promoting amount to the feed of dairy cattle.

Malic acid has also been discovered to improve the feed efficiency response of ruminants. Feed efficiency may be defined as the amount of feed required to produce a unit gain in weight or unit of milk. Increased feed efficiency is, in an era of rapidly rising food costs, an extremely important economic factor in raising animals.

The salts of malic acid are also effective growth-promoting and feed saving agents for ruminants and, additionally, effective milk-promoting agents for female ruminants.

Malic acid can be directly administered to ruminants in the form of tablets, capsules, powders, solutions, suspensions or in admixture with one or more components of the ruminant's diet. Alternatively, malic acid can be administered in the ruminant's drinking water.

It is understood that malic acid will be effective for the purpose delineated herein when used in conjunction with conventional domestic ruminant feeds, including liquid feeds, and/or conventional feed additives that are well known to art skilled persons such as, for example, trenbolone, ronnel, and non-protein nitrogen including urea, biuret and 1,1-diuredo isobutane. Malic acid can also be used in conjunction with antibiotics such as monensin, bacitracines, tylosin, sarimomoicin and tetracyclines, and wormers, anticoccidiols and arsenicals. However, the effectiveness of malic acid as a growth-promoting agent has been found to be greatly minimized when it is administered to ruminants that are on diets that consist primarily of milk or milk derivatives.

The actual growth-promoting amount of malic acid will be dependent upon such factors as the form of preparation, the feed in which the malic acid is employed or the diet of the ruminant and the type of ruminant which is consuming the malic acid. For example, an effective growth-promoting amount for cattle and sheep will generally range from about 25 to about 750 mg/kg animal body weight per day, and preferably from about 50 to about 200 mg/kg body weight per day in the animal feed. As an added feature of this invention, improved feed efficiency in the diets of the ruminants listed above will usually simultaneously be achieved along with improved growth promotion when the ruminants are fed malic acid in an amount within the ranges which are listed above as being effective growth-promoting amounts for the individual ruminant, i.e., generally from about 25 to about 750 mg/kg body weight per day for cattle and sheep.

The milk-promoting amount of malic acid which will be administered to dairy cattle will also depend on factors such as the form of preparation and the feed in which the malic acid is employed or the diet of the animal. Generally, an effective milk-promoting amount for dairy cattle will generally range from about 25 to about 750 mg/kg body weight per day and preferably from about 50 to about 500 mg/kg body weight per day in the dairy cattle feed. Additionally, improved feed efficiency in the diets of dairy cattle will usually simultaneously be achieved along with improved milk promotion when the dairy cattle are fed malic acid in amounts ranging generally from about 25 to about 750 mg/kg body weight per day.

It is understood that, while the ranges delineated above are those that the Applicant considers to be the most optimum for the practice of his invention, the terms "growth-promoting amount" and "milk-promoting amount" can be defined within the spirit of this invention as being those amounts which are less than a toxic amount but are sufficient to produce, respectively, a positive growth-promoting effect in a domestic animal or a positive milk-producing effect in a dairy cow.

EXAMPLES

The following examples are given solely for the purpose of illustration and are not to be construed as limitations of this invention, many variations of which are possible without departing from the spirit or scope thereof.

The DL, or racemic, form of malic acid was used in the following examples. It is understood, however, that the L isomer can also be effectively utilized in the method of the present invention.

EXAMPLE 1

This example utilized three seven-cow groups of Holstein milk cows. Each cow was housed and fed in an individual stall. Group I was fed a diet comprising crude protein concentrate, a grain mixture of ground corn and soybean meal, standard vitamin and mineral supplements, sorghum-sudan forage and approximately 61 mg/kg body weight per day of malic acid. Group II was fed the same diet with approximately 127 mg/kg body weight per day of malic acid. Group III, the control, was fed the same diet without the malic acid. The trial lasted for 28 days. Table 1 indicates the average daily production per cow, over this 28 day period, of milk and solids corrected milk (SCM) and the average daily feed intake per cow for each of the three groups.

TABLE 1

| Group | Milk Produced lbs/day | SCM Produced lbs/day | Average Concentrate Consumed lbs/day | Average Forage Consumed lbs/day |
|---|---|---|---|---|
| I | 35.4 | 32.4 | 18.5 | 77.6 |
| II | 37.8 | 34.0 | 20.2 | 84.8 |
| III | 33.3 | 30.4 | 17.7 | 84.1 |

EXAMPLE 2

In this example, 30 sheep were divided into 5 groups of 6 sheep each. During a 28 day trial period, the sheep were fed the diet which is listed in Table 2. The diets of Groups 2-5 were supplemented by varying amounts of malic acid. Group 1 was a control. Table 3 lists the daily amounts of malic acid consumed for each sheep in the individual groups calculated as mg/kg body weight per day, the average daily weight gain (A.D.G.) and feed intake (F.I.) per sheep per group, the ratio of average feed intake over average weight gain, and the percent change over the control group in the F.I./A.D.G. Ratio. A negative change indicates better feed efficiency.

TABLE 2

| Sheep Diet | |
|---|---|
| Ingredients | Percent (wt.) |
| Straw (Oat) | 30 |
| Hay (Meadow) | 60 |
| Urea | 1.8 |
| Molasses (Cane dried) | 5.0 |
| Salt | 1.0 |
| Dical phosphate | 1.5 |
| Mag Oxide | .6 |
| Sulfur | .1 |
| | 100.0 |
| Percent Crude Protein | 10.9 |

The diet contained a Vitamin A premix.

TABLE 3

| Group | Average Daily Intake Malic Acid/Day mg/kg Body Wt. | A.D.G. (kg) | % Change in A.D.G. Over Control | F.I. (kg) | F.I./A.D.G. | % Change Over Control in F.I./A.D.G. Ratio |
|---|---|---|---|---|---|---|
| 1 | 0 | .114 | — | 1.39 | 12.19 | — |
| 2 | 67 | .158 | +38.9 | 1.47 | 9.30 | −23.7 |
| 3 | 133 | .165 | +44.7 | 1.46 | 8.85 | −27.4 |
| 4 | 200 | .160 | +40.4 | 1.59 | 9.94 | −18.5 |
| 5 | 500 | .152 | +33.3 | 1.42 | 9.34 | −23.4 |

EXAMPLE 3

In this example, 30 beef cattle were divided into five groups of 6 cattle each. During a 112 day trial period, the cattle were fed the diet set forth in Table 4. In addition, various amounts of malic acid were added to feed rations for Groups 2-5. Group 1 was the control. Table 5 lists the average daily weight gain (A.D.G.) per steer for each group and the ratio of average feed intake per steer over average weight gain for each of the five groups.

TABLE 4

| Beef Cattle Diet | |
|---|---|
| Ingredients | Percent (wt.) |
| Ground cobs | 64.9 |
| Ground corn | 30.6 |
| Urea | 2.0 |
| Dical Phosphate | 1.2 |
| Fat | 0.9 |
| Salt | 0.4 |
| | 100% |

The diet also contained trace amounts of minerals and Vitamin A.

TABLE 5

| Group | Average Daily Intake Malic Acid per Steer mg/kg Body Wt. | A.D.G. (kg) | % Change in A.D.G. Over Control | F.I./A.D.G. | % Change Over Control in F.I./A.D.G. Ratio |
|---|---|---|---|---|---|
| 1 | 0 | 1.09 | — | 16.17 | — |
| 2 | 35–50 | 1.34 | +23.0 | 11.56 | −28.5 |
| 3 | 53–75 | 1.16 | +6.4 | 11.27 | −30.3 |
| 4 | 75–100 | 1.37 | +25.7 | 11.67 | −27.8 |
| 5 | 175–200 | 1.18 | +8.2 | 16.68 | +3.2 |

What is claimed is:

1. A method of improving the growth response in ruminants which comprises orally administering to the ruminant a growth-promoting amount of malic acid.

2. The method of claim 1 wherein the ruminants are cattle.

3. The method of claim 2 wherein the growth-promoting amount ranges from about 25 to about 750 milligrams of malic acid per kilogram of cattle body weight per day.

4. The method of claim 2 wherein the growth-promoting amount ranges from about 50 to about 200 milligrams of malic acid per kilogram of cattle body weight per day.

5. The method of claim 1 wherein the ruminants are sheep.

6. The method of claim 5 wherein the growth-promoting amount ranges from about 25 to about 750 milligrams of malic acid per kilogram of sheep body weight per day.

7. The method of claim 5 wherein the growth-promoting amount ranges from about 50 to about 200 milligrams of malic acid per kilogram of sheep body weight per day.

8. A method of improving the milk production in dairy cattle which comprises orally adminstering to said dairy cattle a milk-promoting amount of malic acid.

9. The method of claim 14 wherein the milk-promoting amount ranges from about 25 to about 750 milligrams of malic acid per kilogram of dairy cattle body weight per day.

10. The method of claim 14 wherein the milk-promoting amount ranges from about 50 to about 500 milligrams of malic acid per kilogram of dairy cattle body weight per day.

11. A method of improving the feed efficiency response in a ruminant selected from the group consisting of cattle and sheep which comprises orally administering to the ruminant from about 25 to about 750 milligrams of malic acid per kilogram of ruminant body weight per day.

* * * * *